US008691238B2

(12) United States Patent
Muster et al.

(10) Patent No.: US 8,691,238 B2
(45) Date of Patent: Apr. 8, 2014

(54) HIGH GROWTH REASSORTANT INFLUENZA A VIRUS

(75) Inventors: Thomas Muster, Vienna (AT); Markus Wolschek, Vienna (AT); Andrej Egorov, Vienna (AT); Elisabeth Roethl, Vienna (AT); Julia Romanova, Vienna (AT); Michael Bergmann, Klosterneuburg (AT)

(73) Assignee: Baxter Healthcare SA, Opfikon (CH)

( * ) Notice: Subject to any disclaimer, the term of this patent is extended or adjusted under 35 U.S.C. 154(b) by 60 days.

(21) Appl. No.: 13/140,395

(22) PCT Filed: Dec. 18, 2009

(86) PCT No.: PCT/EP2009/067523

§ 371 (c)(1), (2), (4) Date: Jul. 18, 2011

(87) PCT Pub. No.: WO2010/070098

PCT Pub. Date: Jun. 24, 2010

(65) Prior Publication Data

US 2011/0262481 A1 Oct. 27, 2011

Related U.S. Application Data

(60) Provisional application No. 61/138,819, filed on Dec. 18, 2008.

(30) Foreign Application Priority Data

Mar. 24, 2009 (EP) .................................... 09155992

(51) Int. Cl.
*A61K 39/145* (2006.01)
*A61K 39/12* (2006.01)
*C12N 7/08* (2006.01)

(52) U.S. Cl.
USPC ...................... 424/206.1; 424/205.1; 435/237

(58) Field of Classification Search
None
See application file for complete search history.

(56) References Cited

FOREIGN PATENT DOCUMENTS

| | | |
|---|---|---|
| WO | WO 99/64068 | 12/1999 |
| WO | WO 99/64571 | 12/1999 |
| WO | WO 03/091401 | 11/2003 |
| WO | WO 2008/006780 | 1/2008 |
| WO | WO 2009/007244 | 1/2009 |

OTHER PUBLICATIONS

Romanova J et al. Preclinical evaluation of a replication-deficient intranasal DeltaNS1 H5N1 influenza vaccine. PLoS One. Jun. 19, 2009;4(6):e5984.*
Garcia-Sastre A et al. Influenza A virus lacking the NS1 gene replicates in interferon-deficient systems. Virology. Dec. 20, 1998;252(2):324-30.*
Gao W et al. Protection of mice and poultry from lethal H5N1 avian influenza virus through adenovirus-based immunization. J Virol. Feb. 2006;80(4):1959-64.*
Grimm D et al. Replication fitness determines high virulence of influenza A virus in mice carrying functional Mx1 resistance gene. Proc Natl Acad Sci U S A. Apr. 17, 2007;104(16):6806-11. Epub Apr. 10, 2007.*
Nicolson C et al. Generation of influenza vaccine viruses on Vero cells by reverse genetics: an H5N1 candidate vaccine strain produced under a quality system. Vaccine. Apr. 22, 2005;23(22):2943-52.*
Romanova J et al. Preclinical evaluation of a replication-deficient intranasal DeltaNS1 H5N1 influenza vaccine. PLoS One. Jun. 19, 2009;4(6):e5984. doi: 10.1371/journal.pone.0005984.*
Garcia-Sastre at al. Influenza A virus lacking the NS1 gene replicates in interferon-deficient systems. Virology. Dec. 20, 1998;252(2):324-30.*
Altmüller A et al. Biological and genetic evolution of the nucleoprotein gene of human influenza A viruses. J Gen Virol. Aug. 1989;70 ( Pt 8):2111-9.*
International Search Report for International Application No. PCT/EP2009/067523, Apr. 7, 2010.
Written Opinion of the International Searching Authority for International Application No. PCT/EP2009/067523, Apr. 7, 2010.
Partial European search report, European Patent Application No. 09155992.2, Sep. 8, 2009.
Extended European search report, European Patent Application No. 09155992.2, Nov. 27, 2009.
Nicolson C, et al., "Generation of influenza vaccine viruses on Vero cells by reverse genetics: an H5N1 candidate vaccine strain produced under a quality system," Vaccine (2005) 23: 2943-2952.
Alymova et al., 1998, J Virol, 72:4472-4477.
Couch, 1993, Ann. NY. Acad. Sci, 685:803-812.
Hoffmann et al., 2000, Proc Natl Acad Sci USA, 97:6108-6113.
Horimoto et al., 2006, Vaccine 24:3669-3676.
Salvatore et al., 2002, J Virol, 76:1206-1212.
Steinhauer et al., 1991, PNAS. 88:11525-1152.
Williams et al., 1988, Ann. Intern. Med., 108:616.
International Preliminary Report on Patentability, International Application No. PCT/EP2009/067523, Jun. 21, 2011.

* cited by examiner

*Primary Examiner* — Zachariah Lucas
*Assistant Examiner* — Nick Zou
(74) *Attorney, Agent, or Firm* — Michael Fedrick; Loza & Loza, LLP

(57) ABSTRACT

The present invention provides a high growth reassortant influenza A virus having at least two gene segments of seasonal or pandemic strain origin, a PB1 gene segment of A/Texas/1/77 strain origin and a PA gene segment of A/Puerto Rico/8/34 (H1N1) origin coding for a PA protein comprising at least one amino acid modification at any one of positions 10, 275, 682, according to SEQ ID No. 1. Further provided are vaccine formulations comprising the reassortant influenza A virus of the invention.

17 Claims, 3 Drawing Sheets

C.

D.

E.

HIGH GROWTH REASSORTANT INFLUENZA A VIRUS

CROSS-REFERENCE TO RELATED APPLICATIONS

This application is the U.S. national stage of International Patent Application No. PCT/EP2009/067523, filed on Dec. 18, 2009 and entitled "HIGH GROWTH REASSORTANT INFLUENZA A VIRUS," which claims the benefit of priority from EP Patent Application No. 09155992.2, filed on Mar. 24, 2009, and from U.S. Patent Application No. 61/138,819, filed on Dec. 18, 2008. The disclosures of the foregoing applications are incorporated herein by reference in their entirety.

SEQUENCE LISTING

The entire content of a Sequence Listing titled "Sequence_Listing.txt," created on Jun. 16, 2011 and having a size of 45 kilobytes, which has been submitted in electronic form in connection with the present application, is hereby incorporated by reference herein in its entirety.

FIELD OF THE INVENTION

The present invention provides a high growth reassortant influenza A virus having at least two gene segments of seasonal or pandemic strain origin, a PB1 gene segment of A/Texas/1/77 strain origin and a PA gene segment of A/Puerto Rico/8/34 (H1N1) origin coding for a PA protein comprising amino acid modifications at positions 10, 275, 682, according to SEQ ID No. 1.

Further provided are pharmaceutical compositions comprising the reassortant influenza A virus of the invention.

BACKGROUND OF THE INVENTION

Human influenza virus reference strains have to be prepared when an antigenically new strain is recommended by WHO for being included in the current vaccine formulation. Currently, influenza A strains can be prepared by classic reassortment of the recommended strain and a laboratory strain or by reverse genetics technology wherein the gene segments coding for the surface proteins are derived from the recommended strain and other gene segments are derived from high growth virus strains.

Negative-strand RNA viruses are a group of viruses that comprise several important human pathogens, including influenza, measles, mumps, rabies, respiratory syncytial, Ebola and hantaviruses.

The genomes of these RNA viruses can be unimolecular or segmented, single stranded of (−) polarity. Two essential requirements are shared between these viruses: the genomic RNAs must be efficiently copied into viral RNA, a form which can be used for incorporation into progeny virus particles and transcribed into mRNA which is translated into viral proteins. Eukaryotic host cells typically do not contain a machinery for replicating RNA templates or for translating polypeptides from a negative stranded RNA template. Therefore negative strand RNA viruses encode and carry an RNA-dependent RNA polymerase to catalyze synthesis of new genomic RNA for assembly into progeny and mRNAs for translation into viral proteins.

Genomic viral RNA must be packaged into viral particles in order for the virus to be transmitted. The process by which progeny viral particles are assembled and the protein/protein interactions occur during assembly are similar within the RNA viruses. The formation of virus particles ensures the efficient transmission of the RNA genome from one host cell to another within a single host or among different host organisms.

Virus families containing enveloped single-stranded RNA of the negative-sense genome are classified into groups having non-segmented genomes (Paramyxoviridae, Rhabdoviridae, Filoviridae and Borna Disease Virus, Togaviridae) or those having segmented genomes (Orthomyxoviridae, Bunyaviridae and Arenaviridae). The Orthomyxoviridae family includes the viruses of influenza, types A, B and C viruses, as well as Thogoto and Dhori viruses and infectious salmon anemia virus.

The influenza virions consist of an internal ribonucleoprotein core (a helical nucleocapsid) containing the single-stranded RNA genome, and an outer lipoprotein envelope lined inside by a matrix protein (M1). The segmented genome of influenza A virus consists of eight molecules of linear, negative polarity, single-stranded RNAs which encodes eleven (some influenza A strains ten) polypeptides, including: the RNA-dependent RNA polymerase proteins (PB2, PB1 and PA) and nucleoprotein (NP) which form the nucleocapsid; the matrix membrane proteins (M1, M2); two surface glycoproteins which project from the lipid containing envelope: hemagglutinin (HA) and neuraminidase (NA); the nonstructural protein (NS1) and nuclear export protein (NEP). Most influenza A strains also encode an eleventh protein (PB1-F2) believed to have proapoptotic properties.

Transcription and replication of the genome takes place in the nucleus and assembly occurs via budding on the plasma membrane. The viruses can reassort genes during mixed infections. Influenza virus adsorbs via HA to sialyloligosaccharides in cell membrane glycoproteins and glycolipids. Following endocytosis of the virion, a conformational change in the HA molecule occurs within the cellular endosome which facilitates membrane fusion, thus triggering uncoating. The nucleocapsid migrates to the nucleus where viral mRNA is transcribed. Viral mRNA is transcribed by a unique mechanism in which viral endonuclease cleaves the capped 5'-terminus from cellular heterologous mRNAs which then serve as primers for transcription of viral RNA templates by the viral transcriptase. Transcripts terminate at sites 15 to 22 bases from the ends of their templates, where oligo(U) sequences act as signals for the addition of poly(A) tracts. Of the eight viral RNA molecules so produced, six are monocistronic messages that are translated directly into the proteins representing HA, NA, NP and the viral polymerase proteins, PB2, PB1 and PA. The other two transcripts undergo splicing, each yielding two mRNAs which are translated in different reading frames to produce M1, M2, NS1 and NEP. In other words, the eight viral RNA segments code for eleven proteins: nine structural and 2 nonstructural (NS1 and the recently identified PB1-F2) proteins.

Epidemics and pandemics caused by viral diseases are still claiming human lives and are impacting global economy. Influenza is responsible for millions of lost work days and visits to the doctor, hundreds of thousands of hospitalizations worldwide (Couch 1993, Ann. NY. Acad. Sci 685; 803,), tens of thousands of excess deaths (Collins & Lehmann 1953 Public Health Monographs 213:1; Glezen 1982 Am. J. Public Health 77:712) and billions of Euros in terms of health-care costs (Williams et al. 1988, Ann. Intern. Med. 108:616). When healthy adults get immunized, currently available vaccines prevent clinical disease in 70-90% of cases. This level is reduced to 30-70% in those over the age of 65 and drops still further in those over 65 living in nursing homes (Strategic Perspective 2001: The Antiviral Market. Datamonitor. p. 59).

The virus's frequent antigenic changes further contribute to a large death toll because not even annual vaccination can guarantee protection. Hence, the U.S. death toll rose from 16,363 people in 1976/77 to four times as many deaths in 1998/99 (Wall Street Journal, Flu-related deaths in US despite vaccine researches. Jan. 7, 2003).

Growth of viruses, especially of influenza virus in embryonated chicken eggs have been shown to result in effective production of influenza virus particles which can be either used for production of inactivated or live attenuated influenza virus vaccine strains. Nevertheless during the last years intensive efforts have been made in establishing production systems of virus using cell culture because egg-based method requires a steady supply of specific pathogen-free eggs which could be problematic in case of pandemic. The cell-based technology is an alternative production process that is independent of eggs suppliers and can be started as soon as the seed virus is available. Besides this, inactivated influenza vaccine prepared from the virus grown in mammalian cells was shown to induce more cross-reactive serum antibodies and reveals better protection than egg-grown vaccine (Alymova et al., 1998, *J Virol* 72, 4472-7.).

Nicolson C. et al. (Vaccine, 23, 2005, 2943-2952) described the use of a laboratory strain PR8 strain recommended by WHO and growing to a high titre in eggs as seed virus for vaccine production. Vero cells were used for reverse genetics procedure, cultivation of the virus was performed in eggs or MDCK cells.

WO2009/007244A2 described the development of viral vectors based on influenza virus for the expression of heterologous sequences.

Methods for influenza virus purification was described in WO2008/006780A1 wherein influenza virus reassortment of A/PR8/34 with deletion in NS1 gene and IVR-116 was cultivated on Vero cells and used for purification experiments.

WO 2003/091401A2 described a multi plasmid system for the production of influenza virus.

Generally, in view of the tight timelines from getting access to the influenza strains as recommended by WHO for production of interpandemic or pandemic vaccine compositions and producing said viruses, it is of utmost importance to have virus master strains providing the viral backbone for developing the vaccine virus particles which are of high yield for vaccine production and can be produced in cell culture.

SUMMARY OF THE INVENTION

A high yield reassortant strain based on gene segments derived from IVR116 and A/Puerto Rico/8/34 comprising amino acid modifications which were not comprised in the parental strains in combination with gene segments derived from interpandemic or pandemic virus strains has been developed. The strains can be cultivated under cell culture conditions and show increased growth compared to the parent strains.

The inventive reassortant virus is characterized by comprising at least two gene segments of seasonal or pandemic strain origin, a PB1 gene segment of A/Texas/1/77 strain origin and a PA gene segment of A/Puerto Rico/8/34 (H1N1) origin coding for a PA protein comprising amino acid modifications at positions 10, 275, 682, wherein the amino acid numbering is according to SEQ ID No. 1.

FIGURES

FIG. 1: A. Sequence comparison of HA molecule of original and mutant viruses. Substitutions of two nucleotides (aa) to (tt) by site directed mutagenesis led to the amino acid change K to I at position 58 of HA2 subunit B. Fusion activity of VN1203 and VN1203 K58I viruses with human erythrocytes.

C. Ability to infect cells at pH 5.6 of VN1203 and VN1203 K58I

D. IgA antibody titers in mouse nasal washes after immunization with VN1203 and VN1203 K58I viruses E. HAI antibody titers in mouse sera after immunization with VN1203 and VN1203 K58I viruses

DETAILED DESCRIPTION OF THE INVENTION

Wild-type viruses used in the preparation of the vaccine strains for annual vaccination against epidemic influenza are recommended annually by the World Health Organization (WHO). The regular recurrence of influenza epidemics is caused by antigenic drift, and a number of studies have shown that sufficient changes can accumulate in the virus to allow influenza to reinfect the same host. To address this, influenza vaccine content is reviewed annually to ensure that protection is maintained, despite the emergence of drift variants. These strains are recommended every season and may then be used for the production of reassortant vaccine strains which generally combine the NA and/or HA genes of the wild-type interpandemic or pandemic viruses with the remaining gene segments derived from a master virus (often referred to as a master donor virus or MDV) which will have certain desirable characteristics.

According to the invention the master virus is a reassortant virus comprising gene segments from A/PR8/34 (PR8) and IVR116. IVR116 has been obtained from WHO influenza centres and is well known in influenza vaccine industry.

IVR116 as provided from WHO is comprising gene segments from A/Texas1/77 (H3N2) strain and A/Puerto Rico/8/34 (H1N1) strain.

It has been surprisingly shown that based on these strains the master virus could be developed comprising a PB1 gene segment of A/Texas/1/77 strain origin and a PA gene segment of A/Puerto Rico/8/34 (H1N1) origin comprising specific nucleic acid modifications within the PA gene segment which show increased growth in cell culture.

The PB1 gene is of 2341 nucleotides length and encodes a polypeptide of 759 amino acids.

The PA gene is 2233 nucleotides long and encodes an acidic polymerase protein of 716 amino acids. PA is present in the RNA polymerase complex with PB1 and PB2. According to the invention the PA gene segment of PR8 origin is coding for a PA protein comprising amino acid modification at least of positions 10, 275 and 682, according to the numbering of SEQ ID No. 1 which is the amino acid sequence of the parental A/Puerto Rico 8/34 (H1N1) virus. The modifications can be any amino acid substitutions.

More specifically the PA protein can contain the amino acid substitutions Asn to Ser at position 10 (N10S), amino acid substitution Pro to Leu at position 275 (P275L) and/or amino acid substitution Asp to Asn at position 682 (D682N). According to a specific embodiment the PA protein contains all three substitutions.

The nucleotide sequence of the PA gene can have changes in the nucleotide sequence at any one of nucleotide positions 52-54 (coding for aa 10), 847-849 (coding for aa 275), and 2068-2070 (coding for aa 682) according to SEQ ID. No. 2, which is the nucleic sequence of the unmodified parental PA gene segment. The nucleotide sequence comprising three modifications is incorporated herein as SEQ ID No. 7.

The PA protein can be of following formula (SEQ ID No. 8):

```
MEDFVRQCF(X1)PMIVELAEKTMKEYGEDLKIETNKFAAICTHLEVCF
MYSDFHFINEQGESIIVELGDPNALLKHRFEIIEGRDRTMAWTVVNSIC
NTTGAEKPKFLPDLYDYKENRFIEIGVTRREVHIYYLEKANKIKSEKTH
IHIFSFTGEEMATKADYTLDEESRARIKTRLFTIRQEMASRGLWDSFRQ
SERGEETIEERFEITGTMRKLADQSLPPNFSSLENFRAYVDGFEPNGYI
EGKLSQMSKEVNARIEPFLKTTPRPLRLPNGP(X2)CSQRSKFLLMD
```

ALKLSIEDPSHEGEGIPLYDAIKCMRT-FFGWKEPNVVKPHEKGINPNYLLSWKQVLA ELQDI-ENEEKIPKTKNMKKTSQLKWALGENMA-PEKVDFDDCKDVGDLKQYDSDEPE LRSLASWIQNEFNKACELTDSSWIELD-EIGEDVAPIEHIASMRRNYFTSEVSHCRATE YIMKGVYINTALLNASCAAMDDFQLIP-MISKCRTKEGRRKTNLYGFIIKGRSHLRNDT DVVN-FVSMEFSLTDPRLEPHKWEKYCVLEIGD-MLIRSAIGQVSRPMFLYVRTNGTSK IKMKWGMEMRRCLLQSLQQIESMIE-AESSVKEKDMTKEFFENKSETWPIGESPKGV EES-SIGKVCRTLLAKSVFNSLYASPQLEGF-SAESRKLLLIVQALRDNLEPGTF(X3)LG GLYEAIEECLINDPWVLLNASWFNSFLTHALS, wherein X1 is Ser and X2 is Leu and X3 is Asn The nucleic acid sequence of modified PA comprising the modifications is disclosed in SEQ ID NO. 7.

The term "gene" or "gene segment" is defined in the application as consisting of the complete sequence according to the listed SEQ. Ids. or comprising at least part or fragment thereof that encodes a functional protein.

Additionally the master virus can also comprise the PB2 gene segment derived from IVR116 origin. PB2 gene is 2341 nucleotides long and encodes a polypeptide of 759 amino acids.

More specifically the PB2 polypeptide of the invention can have substituted Val instead of Ile at amino acid position 504 (I504V) and/or Ile instead of Val at amino acid position 560 (V560I) and/or Ser instead of Ala from parental PR8 at amino acid position 84 (A84S) according to the numbering of the sequence shown in SEQ ID. No. 6.

As an alternative embodiment, the master strain can comprise a PB1 gene segment of A/Texas/1/77 strain origin and a PB2 gene segment which show increased growth in cell culture. Specifically the PB2 polypeptide can have substituted Val instead of Ile at amino acid position 504 (I504V) and/or Ile instead of Val at amino acid position 560 (V560I) and/or Ser instead of wt Ala at amino acid position 84 (A84S) according to the numbering of the sequence shown in SEQ ID. No. 6.

The PB2 polypeptide can be of following formula (SEQ ID. No. 6):

MERIKELRNLMSQSRTREILTKTTVDH-MAIIKKYTSGRQEKNPALRMKWMMAMKYPI TADKR ITEMIPERNEQGQTLWSKMND(X1)GSDRVMVS-PLAVTWWNRNGPITNTVHYPKIYK TYFERVERLKH-GTFGPVHFRNQVKIRRRVDINPGHADL-SAKEAQDVIMEVVFPNEV GARILTSESQLTITKEKKEELQDCK-ISPLMVAYMLERELVRKTRFLPVAGGTSSVYIE VLHLTQGTCWEQMYTPGGEVRNDDVDQS-LIIAARNIVRRAAVSADPLASLLEMCHS TQIGGIRM-VDILRQNPTEEQAVDICKAAMGLRISSS-FSFGGFTFKRTSGSSVKREEE VLTGNLQTLKIRVHEGYEEFTMVGRRA-TAILRKATRRLIQLIVSGRDEQSIAEAIIVAM VFSQED-CMIKAVRGDLNFVNRANQRLNPMHQLL-RHFQKDAKVLFQNWGVEPIDNV MGMIGILPDMTPSIEMSMRGVRISK-MGVDEYSSTERVVVSIDRFLR(X2)RDQRGNVL LSPEEVSETQGTEKLTITYSSSMMWE-INGPESVLVNTYQWIIRNWET (X3)KIQWSQNPTM-LYNKMEFEPFQSLVPKAIRGQYSG-FVRTLFQQMRDVLGTFDTA QIIKLLPFAAAPPKQSRMQFSSFTVN-VRGSGMRILVRGNSPVFNYNKATKRLTVLGK DAGTLTEDPDEGTAGVESAVLRGF-LILGKEDKRYGPALSINELSNLAKGEKANVLIG QGD-VVLVMKRKRDSSILTDSQTATKRIRMAIN, wherein X1 is Ser or Arg and/or X2 is Val or Ile and/or X3 is Ile or Val and wherein at least one amino acid X1, X2 or X3 differs from the parental PR8/34 amino acid. Preferably all three amino acid positions are modified compared to the PR8/34 parental strain.

The nucleotide sequence of the PB2 gene is shown in SEQ ID NO 5.

Even more specifically the master virus can comprise an NP protein with at least one amino acid substitution at any one of positions 130, 236 and 452. The amino acid substitutions can be Thr to Met at position 130 (T130M), Lys to Arg at position 236 (K236R), Arg to Lys at position 452 (R452K) according to amino acid positions shown in SEQ ID No. 10 which shows the amino acid sequence of the PR8 parental strain.

As an alternative embodiment, the master strain can comprise a PB1 gene segment of A/Texas/1/77 strain origin and an NP gene segment which show increased growth in cell culture. Specifically the NP polypeptide can contain at least one amino acid substitution at any one of positions 130, 236 and 452. The amino acid substitutions can be Thr to Met at position 130 (T130M), Lys to Arg at position 236 (K236R), Arg to Lys at position 452 (R452K) according to amino acid positions shown in SEQ ID No. 10.

The NP polypeptide can be of following formula (SEQ ID. No. 10):

MASQGTKRSYEQMETDGERQNATEIRAS-VGKMIGGIGRFYIQMCTELKLSDYEGRL IQNSLT IER-MVLSAFDERRNKYLEEHPSAGKDPKKTG-GPIYRRVNGKWMRELILYDKEEIRRI WRQAN NGDDAT(X1)GLTHMMIWHSNLNDATYQRTRALVRT-GMDPRMCSLMQGSTLPRRS GAAGAAVKGVGTM-VMELVRMIKRGINDRNFWRGENGRKTRI-AYERMCNILKGKFQ TAAQ(X2) AMMDQVRESRNPGNAEFEDLTFLARSALILRGS AHKSCLPACVYGPAV ANGYDFEREGYSLVGIDPFR-LLQNSQVYSLIRPNENPAHKSQLVWMACHSAAFEDL RVLSFIKGTKVLPRGKLSTRGVQIAS-NENMETMESSTLELRSRYWAIRTRSGGNTN QQRASAGQISIQPTFSVQRNLPFDRTTI-MAAFNGNTEGRTSDMRTEIIRMMESA(X3) PEDVS-FQGRGVFELSDEKAASPIVPSFDMSNEG-SYFFGDNAEEYDN, wherein X1 is Met or Thr and/or X2 is Arg or Lys and/or X3 is Lys or Arg and wherein at least one amino acid X1, X2 or X3 differs from the parental PR8/34 amino acid. Preferably all three amino acid positions are modified compared to the PR8/34 parental strain.

The NP gene as used in the invention can comprise nucleotide sequence SEQ ID NO. 9.

Having the PB1 gene segment derived from A/Texas/1/77 strain and a PA gene segment comprising at least one of above listed modifications can lead to increased production rates due to better growth and propagation of the virus. It has been shown that the production rates can be increased at least 0.3 logs, preferably 0.5 logs/%, preferably 1 log in cell culture.

Within the scope of the invention, the term "cells" or "cell culture" means the cultivation of individual cells, tissues, organs, insect cells, avian cells, mammalian cells, hybridoma cells, primary cells, continuous cell lines, and/or genetically engineered cells, such as recombinant cells expressing a virus. These can be for example BSC-1 cells, LLC-MK cells, CV-1 cells, CHO cells, COS cells, murine cells, human cells, HeLa cells, 293 cells, VERO cells, MDBK cells, MDCK cells, MDOK cells, CRFK cells, RAF cells, TCMK cells, LLC-PK cells, PK15 cells, WI-38 cells, MRC-5 cells, T-FLY cells, BHK cells, SP2/0 cells, NS0, PerC6 (human retina cells), chicken embryo cells or derivatives, embryonated egg cells, embryonated chicken eggs or derivatives thereof. Preferably the cell line is a VERO cell line.

The term "reassortant," when referring to a virus, indicates that the virus includes genetic and/or polypeptide components derived from more than one parental viral strain or source. For example, a 6:2 reassortant includes 6 genomic segments, most commonly the 6 internal genes from a first parental virus, and two complementary segments, e.g., hemagglutinin and neuraminidase, from a different parental virus.

The master virus of the invention can be an attenuated influenza virus. Specifically the influenza virus comprises deletions or modifications within the pathogenicity factors inhibiting innate immune response of host cells. The attenuation can exemplarily be derived from cold-adapted virus strains or due to a deletion or modification within the NS1 gene (ΔNS1 virus) as described in WO99/64571 and WO99/64068 which are incorporated herein in total by reference. These viruses are replication deficient as they undergo abortive replication in the respiratory tract of animals. Alternatively, the viruses can comprise a deletion or modification of the PB1-F2 gene.

According to the invention the virus can further comprise modifications within the HA gene which can increase the stability of the HA molecule. For example, Steinhauer et al. (1991, PNAS. 88: 11525-1152) identified the K58I mutation in the HA2 of influenza Rostock virus (H7N1) to be responsible for membrane fusion at decreased pH value of compared to the non-mutated virus. This implies that the conformational change of the HA induced by the acidic pH happens in the mutated form of the HA at 0.7 lower pH compared to the wildtype virus. By introducing this mutation to the X-31 influenza virus (H3 subtype) the same effect was shown.

Alternatively, the replication deficient reassortant influenza virus according to the invention can comprise a modified HA protein. This can be a deletion of at least 3 amino acids at the HA cleavage site. Because of the multiple basic amino acids present in the HA can be associated with high virulence, the HA gene can be modified by removal of a stretch of polybasic amino acids at the HA cleavage site as described by Horimoto et al. (Vaccine 24, 3669-76, 2006). Basic amino acids R and K can also be substituted to T to help prevent the reversion to the wild type phenotype. Preferably, the modification can result in as a sequence modification as

| NTPQRERRRKKRGLFGAI<br>A/Vietnam/1203/04 | → | NTPQTETRGLFGAI<br>inventive influenza virus |
|---|---|---|

According to an alternative embodiment of the present invention at least two gene segments, alternatively 3 gene segments can be derived from an H5N1 strain. The H5N1 strain can be any pandemic strain, for example it can be A/Vietnam/1203/04.

According to a specific embodiment of the invention the reassortant influenza A virus is comprising gene segments PB1 of A/Texas/1/77 strain origin, at least one of the segments PB2, PA and/or NP that can be of A/Puerto Rico/8/34 strain origin, wherein the encoded PA polypeptide contains at least one amino acid modification at any one of positions 10, 275, 682, according to SEQ ID No. 1, at least one of the gene segments HA, NA and/or M of a seasonal or pandemic influenza A strain origin and delNS1, having the part or the entire ORF of the NS1 gene deleted, derived from NS1 gene segment of A/Puerto Rico/8/34 strain origin.

Alternatively it can be a reassortant influenza A virus comprising gene segments PB1 of A/Texas/1/77 strain origin, at least one of the segments PB2, PA and/or NP of A/Puerto Rico/8/34 strain origin, wherein the encoded PA polypeptide contains at least one amino acid modification at any one of positions 10, 275, 682, according to SEQ ID No. 1 and at least one of the gene segments HA, NA and/or M of A/Vietnam/1203/04 strain origin and delNS1, having the entire ORF of the NS1 gene deleted, derived from NS1 gene segment of A/Puerto Rico/8/34 strain origin.

According to an embodiment of the invention the reassortant influenza A virus comprises the polynucleotide or at least part thereof encoding PB1 having the nucleotide sequence of SEQ ID NO 3. The PB1 polypeptide encoded by is disclosed in sequence SEQ ID NO 4.

According to the invention the reassortant influenza can comprise an M gene of PR8 origin having the nucleotide sequence SEQ ID NO. 11, encoding an M1 protein comprising amino acid sequence SEQ ID NO. 12 or part thereof and an M2 protein comprising amino acid sequence SEQ ID NO. 13 or part thereof.

According to an alternative embodiment a composition comprising a set of polymerases is covered wherein said polymerases are encoded by a PB1 gene segment of A/Texas/1/77 strain origin, PB2 and PA gene segment of A/Puerto Rico/8/34 (H1N1) origin and wherein the PA protein comprises at least one amino acid modification at positions 10, 275, 682 according to the numbering of SEQ ID No. 1.

Specifically, a reassortant influenza A virus is covered by the invention that comprises

- at least two gene segments of seasonal or pandemic strain origin
- a PB1 gene segment of A/Texas/1/77 strain origin and
- a PA gene segment of A/Puerto Rico/8/34 (PR8) origin coding for a PA protein comprising amino acid modifications N10S, P275L, and D682N according to the numbering of SEQ ID No. 1.
- a PB2 protein comprising amino acids modifications I504V and/or V560I and/or A84S according to the numbering of SEQ ID. No. 6
- a NP protein with amino acid modifications T130M and/or K236R and/or R452K according to the numbering of SEQ ID. No. 10 a NS1 protein comprising a modification, substitution and/or deletion of at least one nucleotide.

Additionally, a pharmaceutical composition, specifically a vaccine comprising the inventive reassortant influenza A virus optionally together with a pharmaceutically acceptable substance is also covered by the invention.

The compositions may be used in methods or as medicaments in preventing, managing, neutralizing, treating and/or ameliorating influenza virus infection. The use of a reassortant influenza virus according to the invention in the manufacture of a medicament for treatment of an influenza virus infection is of course included. The immunogenic compositions may comprise either a live or inactivated influenza A virus of the invention.

The term "pharmaceutically acceptable" means approved by a regulatory agency of the Federal or a state government or listed in the U.S.

The term "carrier" refers to a diluent, adjuvant, excipient, or vehicle with which the pharmaceutical composition (e.g., immunogenic or vaccine formulation) is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should be selected according to the mode of administration. The particular formulation may also depend on whether the virus is live or inactivated.

The term adjuvant refers to a compound or mixture that enhances the immune response to an antigen.

The prophylactic of the immunogenic formulations of the invention is based, in part, upon achieving or inducing an immune response (e.g., a humoral immune response). In one aspect, the immunogenic formulations induce a detectable serum titer of an antibody against antigens of the influenza A virus in either the subject or an animal model thereof (e.g. mouse, ferret, rat or canine model). The serum titer of an anti-body can be determined using techniques known to one of skill in the art, e.g., immunoassays such as ELISAs or hemagglutinin inhibition tests.

A vaccine which is formulated for intranasal delivery is preferred. A method for preventing influenza virus infection of a patient comprising administering the vaccine to a patient is also within the scope of the invention.

EXAMPLES

Example 1

Plasmid Constructions

Influenza A virus GHB01 was generated by classical reassortment of IVR-116 (a high yield reassortant for production in embryonated eggs containing the HA and NA from A/New Caledonia/20/99 (H1N1)) and PR8delNS1 (a derivative of A/Puerto Rico/8/34 strain that does not express NS1 protein, and was passaged multiple times in Vero cells). GHB01 inherited HA and NA segments of A/New Caledonia/20/99, PB1 of A/Texas/1/77 (H3N2) (via IVR-116) while PA, PB2, NP, and M are of PR8 origin (either through PR8delNS1 or IVR-116). All GHB01 segments, except the NS segment lacking NS1, were cloned into the bidirectional expression plasmid pHW2000 (Hoffmann et al. 2000, Proc Natl Acad Sci USA. 97:6108-13). The GHB01 NS segment was cloned into the plasmid pKW2000 to yield the plasmid pKWdelNS1. pKW2000 was obtained by deleting the CMV promoter in pHW2000 (Hoffmann et al. 2000, Proc Natl Acad Sci USA. 97:6108-13). Thus upon transfection only vRNA is transcribed from pKW2000 derivatives.

In addition, PB1 and PB2 of PR8delNS1 were cloned into pHW2000. Compared to GHB01 PB2 PR8delNS1 PB2 comprises two amino acid substitutions (I504V and V560I). GHB01 PA differs from the parent PR8 database sequence at three amino acid positions (N10S, P275L, and D682N).

Virus Generation

Vero cells were maintained in DMEM/F12 medium containing 10% foetal calf serum and 1% Glutamax-I supplement at 37° C. For virus generation seven pHW2000 derivatives containing the segments PA, PB1, PB2, HA, NA, M and NP derived from GHB01 as well as two protein expression plasmids coding for influenza A PR8 NS1 (pCAGGS-NS1 (SAM); (Salvatore et al. 2002, J. Virol. 76:1206-12)) and NEP (pcDNA-NEP) were used together with pKWdelNS1 for cotransfection of Vero cells. Alternatively, PB1 and PB2 plasmids of IVR-116delNS1 were replaced with plasmids derived from PR8delNS1. Following transfection, to support virus replication Vero cells were cultured in serum-free medium (Opti-Pro; Invitrogen) in the presence of 5 μg/ml trypsin.

Titres of both rescued viruses were determined by plaque assay on Vero cells. Titres of the reassortant virus that contained PB1 and PB2 segments derived from IVR-116delNS1 (A/Texas1/77) were found to be about 1 log higher than for the virus that contained PB1 and PB2 from PR8delNS1 (A/Puerto Rico/8/34).

Example 2

A reassortant virus that contained HA and NA of a A/Wisconsin/67/2005 (H1N1)-like strain and the remaining segments of IVR-116delNS1 was adapted to grow (at pH 6.5) on Vero cells. Sequencing revealed three amino acid substitutions in NP (T130M, K236R and R452K) and one amino acid substitution in PB2 (A84S). NP and PB2 segments of the Vero cell-adapted strain were thus cloned into pHW2000. The newly constructed plasmids were used together with PB1, PA, M and delNS1 plasmids derived from IVR-116delNS1 (see example 1) to generate reassortant viruses containing the HA and NA of a A/Wisconsin/67/2005 (H1N1)-like strain or a A/Brisbane/10/2007 (H3N2)-like strain. In parallel reassortant viruses were generated that contained the original IVR-116delNS1 NP and PB2 segments (see example 1). Titres of all viruses were determined by limiting dilution assay. For both, the A/Wisconsin/67/2005 (H1N1)-like and the A/Brisbane/10/2007 (H3N2)-like reassortant viruses titres were found to be about one log higher for the respective strain that contained the modified NP and PB2 segments.

Example 3

Previously we found that H5N1 avian highly pathogenic viruses circulated during last decade do not stand treatment with human nasal wash, having a pH of 5.6. They also did not stand treatment with acidic buffer (pH 5.6) during inoculation of Vero cells. We found that the reason of this instability is high pH at which HA molecule changes the conformation in order to perform fusion with the cell membrane, which for H5N1 virus has the value pH 5.6 while for human viruses it is in the range of 5.2-5.4.

Steinhauer et al., has demonstrated that one substitution in HA2, namely K58I of H7N7 virus could decrease significantly the pH of fusion by 0.7 units. Introduction of this mutation in H3N2 virus had similar effect.

We introduced this change by site-directed mutagenesis to the HA protein of the A/VN1203/04 ΔNS1 (H5N1) virus (reassortant, inheriting the HA, NA, and M genes from A/VN/1203/04, PB1 from A/Texas/1/77, PA gene coding for a protein having modifications N10S, P275L, D682N and the remaining genes from IVR-116 vaccine strain origin in combination with ANS1 gene) and named the rescued virus VN1203 HA K58I (FIG. 1A, Sequence comparison of HA molecule of original and mutant viruses).

HA of both viruses was modified in a trypsin dependent manner. The pH of fusion for mutated virus VN1203 HA K58I was reduced on 0.3 units (FIG. 1B). Moreover, virus VN1203 HA K58I showed reduced loss of infectivity at pH 5.6 (FIG. 1C). FIG. 1B shows the fusion activity of VN1203 and VN1203 K58I viruses with human erythrocytes.

We compared the ability of both viruses to induce the immune response after intranasal immunization of mice. After 4 weeks post immunization mouse sera and nasal washings were obtained and HAI and IgA antibodies were measured. As presented on FIG. 1D, VN1203 HA K58I virus induced 4 times higher titers of IgA antibodies than virus VN1203 with original HA sequence.

---

SEQUENCE LISTING

Figure 1:
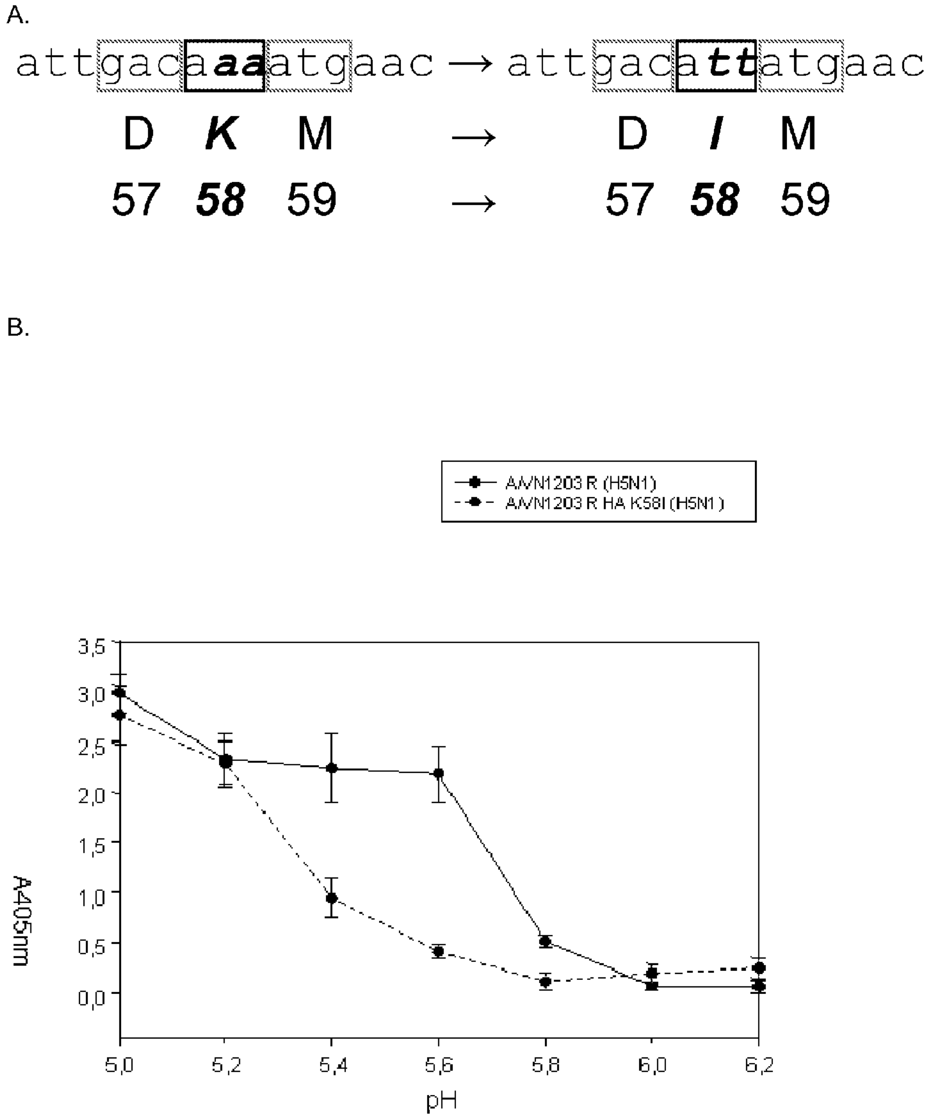
FIG. 1C shows the ability to infect cells at pH 5.6 of VN1203 and VN1203 K58I
FIG. 1D shows IgA antibody titers in mouse nasal washes after immunization with VN1203 and VN1203 K58I viruses
FIG. 1E shows HAI antibody titers in mouse sera after immunization with VN1203 and VN1203 K58I viruses
Figure 1:
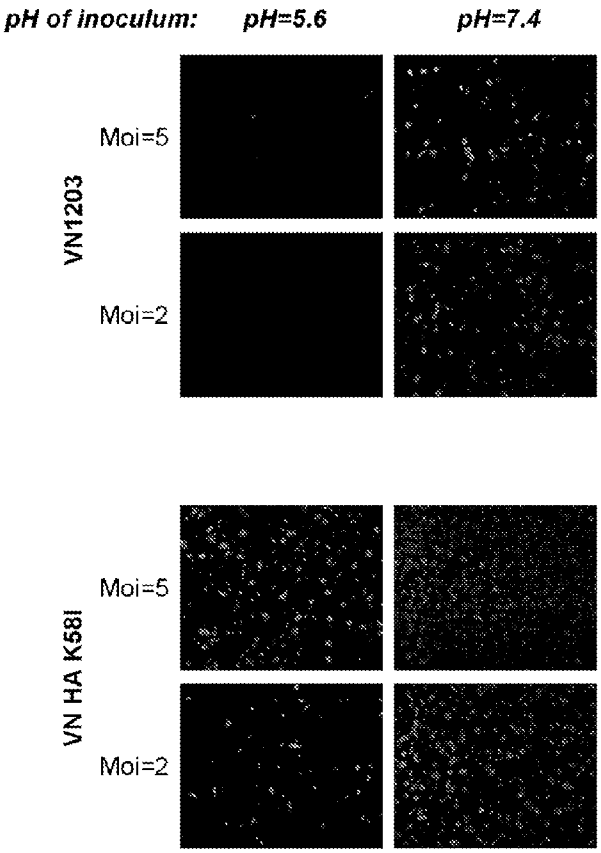
Figure 1:
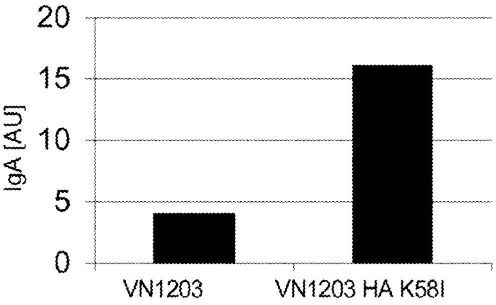
Figure 1:
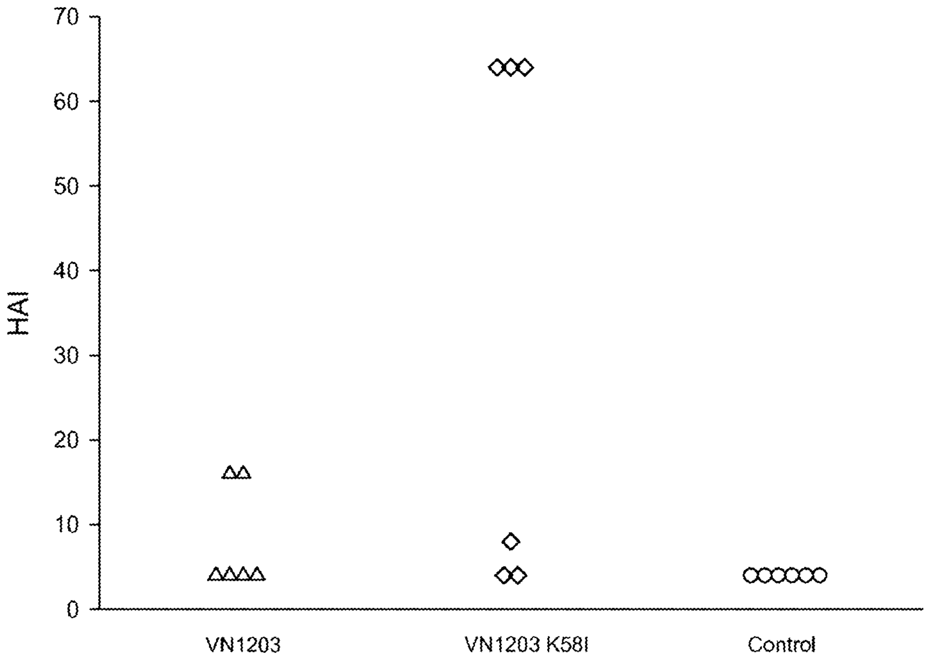

```
<160> NUMBER OF SEQ ID NOS: 13

<210> SEQ ID NO 1
<211> LENGTH: 716
<212> TYPE: PRT
<213> ORGANISM: Influenza A virus

<400> SEQUENCE: 1

Met Glu Asp Phe Val Arg Gln Cys Phe Asn Pro Met Ile Val Glu Leu
1               5                   10                  15

Ala Glu Lys Thr Met Lys Glu Tyr Gly Glu Asp Leu Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Gln Gly Glu Ser Ile Ile Val Glu
    50                  55                  60

Leu Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Ala Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Lys Leu Ala Asp Gln Ser Leu Pro Pro Asn Phe Ser
    210                 215                 220

Ser Leu Glu Asn Phe Arg Ala Tyr Val Asp Gly Phe Glu Pro Asn Gly
225                 230                 235                 240

Tyr Ile Glu Gly Lys Leu Ser Gln Met Ser Lys Glu Val Asn Ala Arg
                245                 250                 255
```

-continued

```
Ile Glu Pro Phe Leu Lys Thr Thr Pro Arg Pro Leu Arg Leu Pro Asn
            260                 265                 270

Gly Pro Pro Cys Ser Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Arg Thr Phe Phe Gly Trp Lys Glu Pro
305                 310                 315                 320

Asn Val Val Lys Pro His Glu Lys Gly Ile Asn Pro Asn Tyr Leu Leu
                325                 330                 335

Ser Trp Lys Gln Val Leu Ala Glu Leu Gln Asp Ile Glu Asn Glu Glu
            340                 345                 350

Lys Ile Pro Lys Thr Lys Asn Met Lys Lys Thr Ser Gln Leu Lys Trp
        355                 360                 365

Ala Leu Gly Glu Asn Met Ala Pro Glu Lys Val Asp Phe Asp Asp Cys
    370                 375                 380

Lys Asp Val Gly Asp Leu Lys Gln Tyr Asp Ser Asp Glu Pro Glu Leu
385                 390                 395                 400

Arg Ser Leu Ala Ser Trp Ile Gln Asn Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ser
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Ile Arg Ser Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Lys Gly Val Glu Glu Ser Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu
        675                 680                 685
```

```
Ala Ile Glu Glu Cys Leu Ile Asn Asp Pro Trp Val Leu Leu Asn Ala
    690                 695                 700

Ser Trp Phe Asn Ser Phe Leu Thr His Ala Leu Ser
705                 710                 715


<210> SEQ ID NO 2
<211> LENGTH: 2233
<212> TYPE: DNA
<213> ORGANISM: Influenza A virus

<400> SEQUENCE: 2

agcgaaagca ggtactgatc caaaatggaa gattttgtgc gacaatgctt caatccgatg     60

attgtcgagc ttgcggaaaa aacaatgaaa gagtatgggg aggacctgaa aatcgaaaca    120

aacaaatttg cagcaatatg cactcacttg gaagtatgct tcatgtattc agattttcac    180

ttcatcaatg agcaaggcga gtcaataatc gtagaacttg gtgatccaaa tgcacttttg    240

aagcacagat ttgaaataat cgagggaaga gatcgcacaa tggcctggac agtagtaaac    300

agtatttgca acactacagg ggctgagaaa ccaaagtttc taccagattt gtatgattac    360

aaggagaata gattcatcga aattggagta acaaggagag aagttcacat atactatctg    420

gaaaaggcca ataaaattaa atctgagaaa acacacatcc acattttctc gttcactggg    480

gaagaaatgg ccacaaaggc agactacact ctcgatgaag aaagcagggc taggatcaaa    540

accagactat tcaccataag acaagaaatg gccagcagag gcctctggga ttcctttcgt    600

cagtccgaga gaggagaaga gacaattgaa gaaaggtttg aaatcacagg aacaatgcgc    660

aagcttgccg accaaagtct cccgccgaac ttctccagcc ttgaaaattt tagagcctat    720

gtggatggat tcgaaccgaa cggctacatt gagggcaagc tgtctcaaat gtccaaagaa    780

gtaaatgcta gaattgaacc tttttgaaa acaacaccac gaccacttag acttccgaat    840

gggcctccct gttctcagcg gtccaaattc ctgctgatgg atgccttaaa attaagcatt    900

gaggacccaa gtcatgaagg agagggaata ccgctatatg atgcaatcaa atgcatgaga    960

acattctttg gatggaagga acccaatgtt gttaaaccac acgaaaaggg aataaatcca   1020

aattatcttc tgtcatggaa gcaagtactg gcagaactgc aggacattga gaatgaggag   1080

aaaattccaa agactaaaaa tatgaagaaa acaagtcagc taaagtgggc acttggtgag   1140

aacatggcac cagaaaaggt agactttgac gactgtaaag atgtaggtga tttgaagcaa   1200

tatgatagtg atgaaccaga attgaggtcg ctagcaagtt ggattcagaa tgagtttaac   1260

aaggcatgcg aactgacaga ttcaagctgg atagagctcg atgagattgg agaagatgtg   1320

gctccaattg aacacattgc aagcatgaga aggaattatt tcacatcaga ggtgtctcac   1380

tgcagagcca cagaatacat aatgaagggg gtgtacatca atactgcctt gcttaatgca   1440

tcttgtgcag caatggatga tttccaatta attccaatga taagcaagtg tagaactaag   1500

gagggaaggc gaaagaccaa cttgtatggt ttcatcataa aaggaagatc ccacttaagg   1560

aatgacaccg acgtggtaaa ctttgtgagc atggagtttt ctctcactga cccaagactt   1620

gaaccacata aatgggagaa gtactgtgtt cttgagatag gagatatgct tataagaagt   1680

gccataggcc aggtttcaag gcccatgttc ttgtatgtga gaacaaatgg aacctcaaaa   1740

attaaaatga aatggggaat ggagatgagg cgttgcctcc tccagtcact tcaacaaatt   1800

gagagtatga ttgaagctga gtcctctgtc aaagagaaag acatgaccaa agagttcttt   1860

gagaacaaat cagaaacatg gcccattgga gagtccccca aggagtggga ggaaagttcc   1920

attgggaagg tctgcaggac tttattagca aagtcggtat tcaacagctt gtatgcatct   1980
```

-continued

```
ccacaactag aaggattttc agctgaatca agaaaactgc ttcttatcgt tcaggctctt   2040

agggacaacc ttgaacctgg gacctttgat cttggggggc tatatgaagc aattgaggag   2100

tgcctgatta atgatccctg ggttttgctt aatgcttctt ggttcaactc cttccttaca   2160

catgcattga gttagttgtg gcagtgctac tatttgctat ccatactgtc caaaaaagta   2220

ccttgtttct act                                                      2233
```

<210> SEQ ID NO 3
<211> LENGTH: 2341
<212> TYPE: DNA
<213> ORGANISM: Influenza A virus

<400> SEQUENCE: 3

```
agcgaaagca ggcaaaccat ttgaatggat gtcaatccga ctttactttt cttgaaaatt     60

ccagcgcaaa atgccataag caccacattc ccttatactg gagatcctcc atacagccat    120

ggaacaggaa caggatacac catggacaca gttaacagaa cacatcaata ttcagaaaaa    180

gggaaatgga caacaaacac agaaactggg gcgccccaac ttaacccgat tgatggacca    240

ctacctgagg ataatgagcc aagtggatat gcacaaacag actgtgtcct ggaagctatg    300

gctttccttg aggaatccca cccagggatc tttgaaaact cgtgccttga aacaatggaa    360

gtcgttcaac aaacaagagt ggacagactg acccaaggtc gtcagaccta tgattggaca    420

ttaaacagaa atcaaccagc cgcaactgca ttagccaaca ctatagaagt tttcagatcg    480

aatggtctaa cagctaatga gtcgggaagg ctaatagatt tcctcaagga tgtgatggaa    540

tcaatggata aagaggaaat agagataaca acacacttcc aaagaaaaag aagagtaaga    600

gacaacatga ccaagaaaat ggtcacacaa agaacaatag gaaagaaaaa gcagagagtg    660

aacaagagaa gctatctaat aagagcatta actttgaaca caatgaccaa agatgcagaa    720

agaggtaaat taaagagaag agctattgca acacccggga tgcaaatcag agggttcgtg    780

tactttgttg aaactctagc taggagcatt tgtgagaagc ttgaacagtc tggacttcca    840

gtaggaggta atgaaaagaa ggccaaactg gcaaatgttg tgagaaagat gatgactaat    900

tcacaagaca cagagctttc tttcacaatt actggagaca atactaagtg gaatgaaaat    960

caaaatcctc gaatgttcct ggcgatgatt acatatatca caaaaaatca acctgaatgg   1020

ttcagaaaca tcctgagcat cgcacccata atgttctcaa acaaaatggc gagactaggg   1080

aaaggataca tgttcgaaag taagagaatg aagctccgaa cacaaatacc agcagaaatg   1140

ctagcaagca ttgacctaaa gtatttcaat gaatcaacaa gaaagaaaat tgagaaaata   1200

aggcctcttc taatagatgg cacagcgtca ttgagccctg gaatgatgat gggcatgttc   1260

aacatgctaa gtacggtttt aggagtctca atactgaatc ttgggcaaaa gaaatacacc   1320

aaaacaacat actggtggga tgggcttcaa tcctctgatg attttgctct catagtgaat   1380

gcaccaaatc atgagggaat acaagcagga gtggatagat tctacagaac ctgcaagcta   1440

gtcggaatca atatgagcaa gaagaagtcc tatataaata ggacaggaac atttgaattc   1500

acaagctttt tttatcgcta tggatttgtg gccaatttta gcatggagct gcccagtttt   1560

ggagtgtctg ggattaatga atcagctgat atgagcattg gagtaacagt gataaagaac   1620

aacatgataa acaatgacct tggaccagca acagcccaga tggctcttca actgttcatc   1680

aaggactaca gatatacata tcggtgccac agaggagaca cacaaattca gacgaggaga   1740

tcatttgagc taaagaagct gtgggagcaa acccgatcaa aggcaggact attggtttca   1800

gatggaggac cgaacttata caatatccgg aatcttcaca tccctgaagt ctgcttaaag   1860
```

-continued

```
tgggagctaa tggatgaaga ctatcaggga agactttgta atcccctgaa tccatttgtc   1920

agccataaag agattgagtc tgtaaacaat gctgtggtaa tgccagctca tggtccagcc   1980

aagagcatgg aatatgacgc tgttgcaact acacactcct ggattcccaa gaggaaccgc   2040

tctattctca acacaagcca aaggggaatt cttgaggatg aacagatgta tcagaagtgc   2100

tgcaacctgt tcgagaaatt tttccccagt agttcataca ggagaccggt tggaatttcc   2160

agcatggtgg aggccatggt gtctagggcc cggattgatg ccagaattga cttcgagtct   2220

ggacggatta agaaagaaga gttctccgag atcatgaaga tctgttccac cattgaagag   2280

ctcagacggc aaaaacaatg aatttagctt gtccttcatg aaaaaatgcc ttgtttctac   2340

t                                                                   2341
```

<210> SEQ ID NO 4
<211> LENGTH: 758
<212> TYPE: PRT
<213> ORGANISM: Influenza A virus

<400> SEQUENCE: 4

```
Met Asp Val Asn Pro Thr Leu Leu Phe Leu Lys Ile Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Val Gln Gln Thr Arg Val Asp Arg Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Glu Glu Ile Glu Ile Thr Thr His Phe Gln Arg Lys Arg Arg Val Arg
            180                 185                 190

Asp Asn Met Thr Lys Lys Met Val Thr Gln Arg Thr Ile Gly Lys Lys
        195                 200                 205

Lys Gln Arg Val Asn Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285
```

-continued

```
Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Lys Asn Gln Pro Glu Trp Phe Arg Asn Ile
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Arg Met Lys Leu Arg Thr Gln Ile
        355                 360                 365

Pro Ala Glu Met Leu Ala Ser Ile Asp Leu Lys Tyr Phe Asn Glu Ser
    370                 375                 380

Thr Arg Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Lys Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Glu Gln Thr Arg Ser Lys Ala Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Gln Gly Arg Leu
    610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
```

-continued

```
705                 710                 715                 720

Arg Ala Arg Ile Asp Ala Arg Ile Asp Phe Glu Ser Gly Arg Ile Lys
                725                 730                 735

Lys Glu Glu Phe Ser Glu Ile Met Lys Ile Cys Ser Thr Ile Glu Glu
            740                 745                 750

Leu Arg Arg Gln Lys Gln
        755


<210> SEQ ID NO 5
<211> LENGTH: 2341
<212> TYPE: DNA
<213> ORGANISM: Influenza A virus

<400> SEQUENCE: 5

agcgaaagca ggtcaattat attcaatatg gaaagaataa aagaactacg aaatctaatg     60

tcgcagtctc gcacccgcga gatactcaca aaaaccaccg tggaccatat ggccataatc    120

aagaagtaca catcaggaag acaggagaag aacccagcac ttaggatgaa atggatgatg    180

gcaatgaaat atccaattac agcagacaag aggataacgg aaatgattcc tgagagaaat    240

gagcaaggac aaactttatg gagtaaaatg aatgatgccg gatcagaccg agtgatggta    300

tcacctctgg ctgtgacatg gtggaatagg aatggaccaa taacaaatac agttcattat    360

ccaaaaatct acaaaactta ttttgaaaga gtcgaaaggc taaagcatgg aacctttggc    420

cctgtccatt ttagaaacca agtcaaaata cgtcggagag ttgacataaa tcctggtcat    480

gcagatctca gtgccaagga ggcacaggat gtaatcatgg aagttgtttt ccctaacgaa    540

gtgggagcca ggatactaac atcggaatcg caactaacga taaccaaaga gaagaaagaa    600

gaactccagg attgcaaaat ttctcctttg atggttgcat acatgttgga gagagaactg    660

gtccgcaaaa cgagattcct cccagtggct ggtggaacaa gcagtgtgta cattgaagtg    720

ttgcatttga ctcaaggaac atgctgggaa cagatgtata ctccaggagg ggaagtgagg    780

aatgatgatg ttgatcaaag cttgattatt gctgctagga acatagtgag aagagctgca    840

gtatcagcag atccactagc atctttattg gagatgtgcc acagcacaca gattggtgga    900

attaggatgg tagacatcct taggcagaac ccaacagaag agcaagccgt ggatatatgc    960

aaggctgcaa tgggactgag aattagctca tccttcagtt ttggtggatt cacatttaag   1020

agaacaagcg gatcatcagt caagagagag gaagaggtgc ttacgggcaa tcttcaaaca   1080

ttgaagataa gagtgcatga gggatatgaa gagttcacaa tggttgggag aagagcaaca   1140

gccatactca gaaaagcaac caggagattg attcagctga tagtgagtgg gagagacgaa   1200

cagtcgattg ccgaagcaat aattgtggcc atggtatttt cacaagagga ttgtatgata   1260

aaagcagtca gaggtgatct gaatttcgtc aatagggcga atcaacgatt gaatcctatg   1320

catcaacttt taagacattt tcagaaggat gcgaaagtgc tttttcaaaa ttggggagtt   1380

gaacctatcg acaatgtgat gggaatgatt gggatattgc ccgacatgac tccaagcatc   1440

gagatgtcaa tgagaggagt gagaatcagc aaaatgggtg tagatgagta ctccagcacg   1500

gagagggtag tggtgagcat tgaccgtttt ttgagaatcc gggaccaacg aggaaatgta   1560

ctactgtctc ccgaggaggt cagtgaaaca cagggaacag agaaactgac aataacttac   1620

tcatcgtcaa tgatgtggga gattaatggt cctgaatcag tgttggtcaa tacctatcaa   1680

tggatcatca gaaactggga aactgttaaa attcagtggt cccagaaccc tacaatgcta   1740

tacaataaaa tggaatttga accatttcag tctttagtac ctaaggccat tagaggccaa   1800

tacagtgggt ttgtaagaac tctgttccaa caaatgaggg atgtgcttgg gacatttgat   1860
```

-continued

```
accgcacaga taataaaact tcttcccttc gcagccgctc caccaaagca aagtagaatg   1920

cagttctcct catttactgt gaatgtgagg ggatcaggaa tgagaatact tgtaaggggc   1980

aattctcctg tattcaacta taacaaggcc acgaagagac tcacagttct cggaaaggat   2040

gctggcactt taactgaaga cccagatgaa ggcacagctg gagtggagtc cgctgttctg   2100

aggggattcc tcattctggg caaagaagac aagagatatg ggccagcact aagcatcaat   2160

gaactgagca accttgcgaa aggagagaag gctaatgtgc taattgggca aggagacgtg   2220

gtgttggtaa tgaaacggaa acgggactct agcatactta ctgacagcca gacagcgacc   2280

aaaagaattc ggatggccat caattagtgt cgaatagttt aaaaacgacc ttgtttctac   2340

t                                                                   2341
```

<210> SEQ ID NO 6
<211> LENGTH: 759
<212> TYPE: PRT
<213> ORGANISM: Influenza A virus

<400> SEQUENCE: 6

```
Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Thr
    50                  55                  60

Glu Met Ile Pro Glu Arg Asn Glu Gln Gly Gln Thr Leu Trp Ser Lys
65                  70                  75                  80

Met Asn Asp Ala Gly Ser Asp Arg Val Met Val Ser Pro Leu Ala Val
                85                  90                  95

Thr Trp Trp Asn Arg Asn Gly Pro Ile Thr Asn Thr Val His Tyr Pro
            100                 105                 110

Lys Ile Tyr Lys Thr Tyr Phe Glu Arg Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ser Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
        275                 280                 285
```

```
Ile Gly Gly Ile Arg Met Val Asp Ile Leu Arg Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Val Leu Thr Gly Asn Leu Gln Thr Leu
            340                 345                 350

Lys Ile Arg Val His Glu Gly Tyr Glu Glu Phe Thr Met Val Gly Arg
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Val Glu Pro Ile Asp Asn Val Met Gly Met Ile Gly Ile Leu
    450                 455                 460

Pro Asp Met Thr Pro Ser Ile Glu Met Ser Met Arg Gly Val Arg Ile
465                 470                 475                 480

Ser Lys Met Gly Val Asp Glu Tyr Ser Ser Thr Glu Arg Val Val Val
                485                 490                 495

Ser Ile Asp Arg Phe Leu Arg Ile Arg Asp Gln Arg Gly Asn Val Leu
            500                 505                 510

Leu Ser Pro Glu Glu Val Ser Glu Thr Gln Gly Thr Glu Lys Leu Thr
        515                 520                 525

Ile Thr Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Thr Val
545                 550                 555                 560

Lys Ile Gln Trp Ser Gln Asn Pro Thr Met Leu Tyr Asn Lys Met Glu
                565                 570                 575

Phe Glu Pro Phe Gln Ser Leu Val Pro Lys Ala Ile Arg Gly Gln Tyr
            580                 585                 590

Ser Gly Phe Val Arg Thr Leu Phe Gln Gln Met Arg Asp Val Leu Gly
        595                 600                 605

Thr Phe Asp Thr Ala Gln Ile Ile Lys Leu Leu Pro Phe Ala Ala Ala
    610                 615                 620

Pro Pro Lys Gln Ser Arg Met Gln Phe Ser Ser Phe Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
            660                 665                 670

Gly Thr Leu Thr Glu Asp Pro Asp Glu Gly Thr Ala Gly Val Glu Ser
        675                 680                 685

Ala Val Leu Arg Gly Phe Leu Ile Leu Gly Lys Glu Asp Lys Arg Tyr
    690                 695                 700

Gly Pro Ala Leu Ser Ile Asn Glu Leu Ser Asn Leu Ala Lys Gly Glu
```

-continued

```
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755


<210> SEQ ID NO 7
<211> LENGTH: 2341
<212> TYPE: DNA
<213> ORGANISM: Influenza A virus

<400> SEQUENCE: 7

agcgaaagca ggcaaaccat ttgaatggat gtcaatccga ctttactttt cttgaaaatt     60

ccagcgcaaa atgccataag caccacattc ccttatactg gagatcctcc atacagccat    120

ggaacaggaa caggatacac catggacaca gttaacagaa cacatcaata ttcagaaaaa    180

gggaaatgga caacaaacac agaaactggg gcgccccaac ttaacccgat tgatggacca    240

ctacctgagg ataatgagcc aagtggatat gcacaaacag actgtgtcct ggaagctatg    300

gctttccttg aggaatccca cccagggatc tttgaaaact cgtgccttga aacaatggaa    360

gtcgttcaac aaacaagagt ggacagactg acccaaggtc gtcagaccta tgattggaca    420

ttaaacagaa atcaaccagc cgcaactgca ttagccaaca ctatagaagt tttcagatcg    480

aatggtctaa cagctaatga gtcgggaagg ctaatagatt tcctcaagga tgtgatggaa    540

tcaatggata aagaggaaat agagataaca acacacttcc aaagaaaaag aagagtaaga    600

gacaacatga ccaagaaaat ggtcacacaa agaacaatag gaaagaaaaa gcagagagtg    660

aacaagagaa gctatctaat aagagcatta actttgaaca caatgaccaa agatgcagaa    720

agaggtaaat taaagagaag agctattgca acacccggga tgcaaatcag agggttcgtg    780

tactttgttg aaactctagc taggagcatt tgtgagaagc ttgaacagtc tggacttcca    840

gtaggaggta atgaaaagaa ggccaaactg gcaaatgttg tgagaaagat gatgactaat    900

tcacaagaca cagagctttc tttcacaatt actggagaca atactaagtg gaatgaaaat    960

caaaatcctc gaatgttcct ggcgatgatt acatatatca caaaaaatca acctgaatgg   1020

ttcagaaaca tcctgagcat cgcacccata atgttctcaa acaaaatggc gagactaggg   1080

aaaggataca tgttcgaaag taagagaatg aagctccgaa cacaaatacc agcagaaatg   1140

ctagcaagca ttgacctaaa gtatttcaat gaatcaacaa gaaagaaaat tgagaaaata   1200

aggcctcttc taatagatgg cacagcgtca ttgagccctg gaatgatgat gggcatgttc   1260

aacatgctaa gtacggtttt aggagtctca atactgaatc ttgggcaaaa gaaatacacc   1320

aaaacaacat actggtggga tggcttcaa tcctctgatg attttgctct catagtgaat   1380

gcaccaaatc atgagggaat acaagcagga gtggatagat tctacagaac ctgcaagcta   1440

gtcggaatca atatgagcaa gaagaagtcc tatataaata ggacaggaac atttgaattc   1500

acaagctttt tttatcgcta tggatttgtg gccaatttta gcatggagct gcccagtttt   1560

ggagtgtctg ggattaatga atcagctgat atgagcattg gagtaacagt gataaagaac   1620

aacatgataa acaatgacct tggaccagca acagcccaga tggctcttca actgttcatc   1680

aaggactaca gatatacata tcggtgccac agaggagaca cacaaattca gacgaggaga   1740

tcatttgagc taaagaagct gtgggagcaa acccgatcaa aggcaggact attggtttca   1800

gatggaggac cgaacttata caatatccgg aatcttcaca tccctgaagt ctgcttaaag   1860
```

-continued tgggagctaa tggatgaaga ctatcaggga agactttgta atcccctgaa tccatttgtc 1920
agccataaag agattgagtc tgtaaacaat gctgtggtaa tgccagctca tggtccagcc 1980
aagagcatgg aatatgacgc tgttgcaact acacactcct ggattcccaa gaggaaccgc 2040
tctattctca acacaagcca aaggggaatt cttgaggatg aacagatgta tcagaagtgc 2100
tgcaacctgt tcgagaaatt tttccccagt agttcataca ggagaccggt tggaatttcc 2160
agcatggtgg aggccatggt gtctagggcc cggattgatg ccagaattga cttcgagtct 2220
ggacggatta agaaagaaga gttctccgag atcatgaaga tctgttccac cattgaagag 2280
ctcagacggc aaaaacaatg aatttagctt gtccttcatg aaaaaatgcc ttgtttctac 2340
t 2341

<210> SEQ ID NO 8
<211> LENGTH: 2233
<212> TYPE: DNA
<213> ORGANISM: Influenza A virus

<400> SEQUENCE: 8
agcgaaagca ggtactgatc caaaatggaa gattttgtgc gacaatgctt cagtccgatg 60
attgtcgagc ttgcggaaaa aacaatgaaa gagtatgggg aggacctgaa aatcgaaaca 120
aacaaatttg cagcaatatg cactcacttg gaagtatgct tcatgtattc agattttcac 180
ttcatcaatg agcaaggcga gtcaataatc gtagaacttg gtgatccaaa tgcacttttg 240
aagcacagat ttgaaataat cgagggaaga gatcgcacaa tggcctggac agtagtaaac 300
agtatttgca acactacagg ggctgagaaa ccaaagttcc taccagattt gtatgattac 360
aaggagaata gattcatcga aattggagta acaaggagag aagttcacat atactatctg 420
gaaaaggcca ataaaattaa atctgagaaa acacacatcc acatttctc gttcactggg 480 gaagaaatgg ccacaaaggc agactacact ctcgatgaag aaagcagggc taggatcaaa 540
accagactat tcaccataag acaagaaatg gccagcagag gcctctggga ttcctttcgt 600
cagtccgaga gaggagaaga gacaattgaa gaaaggtttg aaatcacagg aacaatgcgc 660
aagcttgccg accaaagtct cccgccgaac ttctccagcc ttgaaaattt tagagcctat 720
gtggatggat tcgaaccgaa cggctacatt gagggcaagc tgtctcaaat gtccaaagaa 780
gtaaatgcta gaattgaacc tttttgaaa acaacaccac gaccacttag acttccgaat 840
gggcctctct gttctcagcg gtccaaattc ctgctgatgg atgccttaaa attaagcatt 900
gaggacccaa gtcatgaagg agagggaata ccgctatatg atgcaatcaa atgcatgaga 960
acattctttg gatggaagga acccaatgtt gttaaaccac acgaaaaggg aataaatcca 1020
aattatcttc tgtcatggaa gcaagtactg gcagaactgc aggacattga gaatgaggag 1080
aaaattccaa agactaaaaa tatgaagaaa acaagtcagc taaagtgggc acttggtgag 1140
aacatggcac cagaaaaggt agactttgac gactgtaaag atgtaggtga tttgaagcaa 1200
tatgatagtg atgaaccaga attgaggtcg cttgcaagtt ggattcagaa tgagtttaac 1260
aaggcatgcg aactgacaga ttcaagctgg atagagctcg atgagattgg agaagatgtg 1320
gctccaattg aacacattgc aagcatgaga aggaattatt tcacatcaga ggtgtctcac 1380
tgcagagcca cagaatacat aatgaagggg gtgtacatca atactgcctt gcttaatgca 1440
tcttgtgcag caatggatga tttccaatta attccaatga taagcaagtg tagaactaag 1500
gagggaaggc gaaagaccaa cttgtatggt ttcatcataa aaggaagatc ccacttaagg 1560
aatgacaccg acgtggtaaa ctttgtgagc atggagtttt ctctcactga cccaagactt 1620
gaaccacata aatgggagaa gtactgtgtt cttgagatag gagatatgct tataagaagt 1680
gccataggcc aggtttcaag gcccatgttc ttgtatgtga gaacaaatgg aacctcaaaa 1740
attaaaatga aatggggaat ggagatgagg cgttgcctcc tccagtcact tcaacaaatt 1800
gagagtatga ttgaagctga gtcctctgtc aaagagaaag acatgaccaa agagttcttt 1860
gagaacaaat cagaaacatg gcccattgga gagtccccca aaggagtgga ggaaagttcc 1920
attgggaagg tctgcaggac tttattagca aagtcggtat tcaacagctt gtatgcatct 1980
ccacaactag aaggattttc agctgaatca agaaaactgc ttcttatcgt tcaggctctt 2040
agggacaacc ttgaacctgg gacctttaat cttgggggc tatatgaagc aattgaggag 2100
tgcctgatta atgatccctg ggttttgctt aatgcttctt ggttcaactc cttccttaca 2160
catgcattga gttagttgtg gcagtgctac tatttgctat ccatactgtc caaaaaagta 2220
ccttgtttct act 2233

<210> SEQ ID NO 9
<211> LENGTH: 1565
<212> TYPE: DNA
<213> ORGANISM: Influenza A virus

<400> SEQUENCE: 9
agcaaaagca gggtagataa tcactcactg agtgacatca aaatcatggc gtcccaaggc 60
accaaacggt cttacgaaca gatggagact gatggagaac gccagaatgc cactgaaatc 120
agagcatccg tcggaaaaat gattggtgga attggacgat tctacatcca aatgtgcacc 180
gaactcaaac tcagtgatta tgagggacgg ttgatccaaa acagcttaac aatagagaga 240
atggtgctct ctgcttttga cgaaaggaga aataaatacc tggaagaaca tcccagtgcg 300
gggaaagatc ctaagaaaac tggaggacct atatacagga gagtaaacgg aaagtggatg 360
agagaactca tcctttatga caaagaagaa ataaggcgaa tctggcgcca agctaataat 420
ggtgacgatg caacggctgg tctgactcac atgatgatct ggcattccaa tttgaatgat 480
gcaacttatc agaggacaag agctcttgtt cgcaccggaa tggatcccag gatgtgctct 540
ctgatgcaag gttcaactct ccctaggagg tctggagccg caggtgctgc agtcaaagga 600
gttggaacaa tggtgatgga attggtcagg atgatcaaac gtgggatcaa tgatcggaac 660
ttctggaggg gtgagaatgg acgaaaaaca agaattgctt atgaaagaat gtgcaacatt 720
ctcaaaggga aatttcaaac tgctgcacaa aaagcaatga tggatcaagt gagagagagc 780
cggaacccag ggaatgctga gttcgaagat ctcacttttc tagcacggtc tgcacttata 840
ttgagagggt cggttgctca caagtcctgc ctgcctgcct gtgtgtatgg acctgccgta 900
gccaatgggt acgactttga aagagaggga tactctctag tcggaataga ccctttcaga 960
ctgcttcaaa acagccaagt gtacagccta atcagaccaa atgagaatcc agcacacaag 1020
agtcaactgg tgtggatggc atgccattct gccgcatttg aagatctaag agtattaagc 1080
ttcatcaaag ggacgaaggt gctcccaaga gggaagcttt ccactagagg agttcaaatt 1140
gcttccaatg aaaatatgga gactatggaa tcaagtacac ttgaactgag aagcaggtac 1200
tgggccataa ggaccagaag tggaggaaac accaatcaac agagggcatc tgcgggccaa 1260
atcagcatac aacctacgtt ctcagtacag agaaatctcc cttttgacag aacaaccatt 1320
atggcagcat tcaatgggaa tacagagggg agaacatctg acatgaggac cgaaatcata 1380
aggatgatgg aaagtgcaag accagaagat gtgtctttcc aggggcgggg agtcttcgag 1440
ctctcggacg aaaaggcagc gagcccgatc gtgccttcct ttgacatgag taatgaagga 1500

```
tcttatttct tcggagacaa tgcagaggag tacgacaatt aaagaaaaat acccttgttt   1560

ctact                                                                1565


<210> SEQ ID NO 10
<211> LENGTH: 498
<212> TYPE: PRT
<213> ORGANISM: Influenza A virus

<400> SEQUENCE: 10

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Phe Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Asn Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Ser Phe Ile Lys Gly Thr Lys Val
            340                 345                 350

Leu Pro Arg Gly Lys Leu Ser Thr Arg Gly Val Gln Ile Ala Ser Asn
```

```
        355                 360                 365

Glu Asn Met Glu Thr Met Glu Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Ile Met Ala Ala Phe Asn Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn


<210> SEQ ID NO 11
<211> LENGTH: 1027
<212> TYPE: DNA
<213> ORGANISM: Influenza A virus

<400> SEQUENCE: 11

agcgaaagca ggtagatatt gaaagatgag tcttctaacc gaggtcgaaa cgtacgtact      60

ctctatcatc ccgtcaggcc ccctcaaagc cgagatcgca cagagacttg aagatgtctt     120

tgcagggaag aacaccgatc ttgaggttct catggaatgg ctaaagacaa gaccaatcct     180

gtcacctctg actaagggga ttttaggatt tgtgttcacg ctcaccgtgc ccagtgagcg     240

aggactgcag cgtagacgct ttgtccaaaa tgcccttaat gggaacgggg atccaaataa     300

catggacaaa gcagttaaac tgtataggaa gctcaagagg gagataacat tccatggggc     360

caaagaaatc tcactcagtt attctgctgg tgcacttgcc agttgtatgg gcctcatata     420

caacaggatg gggactgtga ccactgaagt ggcatttggc ctagtatgtg caacctgtga     480

acagattgct gactcccagc atcggtctca taggcaaatg gttacaacaa ccaatccact     540

aatcagacat gagaacagaa tggttttagc cagcactaca gctaaggcta tggagcaaat     600

ggctggatcg agtgagcaag cagcagaggc catggaggtt gctagtcagg ctagacaaat     660

ggtgcaagcg atgagaacca ttgggactca tcctagctcc agtgctggtc tgaaaaatga     720

tcttcttgaa aatttgcagg cctatcagaa acgaatgggg gtgcagatgc aacggttcaa     780

gtgatcctct cactattgcc gcaaatatca ttgggatctt gcacttgaca ttgtggattc     840

ttgatcgtct ttttttcaaa tgcatttacc gtcgctttaa atacggactg aaaggagggc     900

cttctacgga aggagtgcca aagtctatga gggaagaata tcgaaaggaa cagcagagtg     960

ctgtggatgc tgacgatggt cattttgtca gcatagagct ggagtaaaaa actaccttgt    1020

ttctact                                                              1027


<210> SEQ ID NO 12
<211> LENGTH: 252
<212> TYPE: PRT
<213> ORGANISM: Influenza A virus

<400> SEQUENCE: 12
```

-continued

```
Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Val Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ser Leu Ser Tyr Ser Ala Gly Ala Leu Ala Ser Cys Met
        115                 120                 125

Gly Leu Ile Tyr Asn Arg Met Gly Thr Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Thr Ile Gly Thr His Pro Ser
    210                 215                 220

Ser Ser Ala Gly Leu Lys Asn Asp Leu Leu Glu Asn Leu Gln Ala Tyr
225                 230                 235                 240

Gln Lys Arg Met Gly Val Gln Met Gln Arg Phe Lys
                245                 250


<210> SEQ ID NO 13
<211> LENGTH: 97
<212> TYPE: PRT
<213> ORGANISM: Influenza A virus

<400> SEQUENCE: 13

Met Ser Leu Leu Thr Glu Val Glu Thr Pro Ile Arg Asn Glu Trp Gly
1               5                   10                  15

Cys Arg Cys Asn Gly Ser Ser Asp Pro Leu Thr Ile Ala Ala Asn Ile
            20                  25                  30

Ile Gly Ile Leu His Leu Thr Leu Trp Ile Leu Asp Arg Leu Phe Phe
        35                  40                  45

Lys Cys Ile Tyr Arg Arg Phe Lys Tyr Gly Leu Lys Gly Gly Pro Ser
    50                  55                  60

Thr Glu Gly Val Pro Lys Ser Met Arg Glu Glu Tyr Arg Lys Glu Gln
65                  70                  75                  80

Gln Ser Ala Val Asp Ala Asp Asp Gly His Phe Val Ser Ile Glu Leu
                85                  90                  95

Glu
```

The invention claimed is:

1. A reassortant influenza A virus characterized in that it comprises:

at least two gene segments of seasonal or pandemic strain origin;

a PB1 gene segment of A/Texas/1/77 strain origin;

a PA gene segment of A/Puerto Rico/8/34 (PR8) origin coding for a PA protein amino acid modifications at positions 10, 275, and 682, according to the numbering of SEQ ID NO:1; and a NP protein that has at least one amino acid substitution at any one of positions 130, 236 and 452 according to the numbering of SEQ ID NO: 10.

2. A reassortant influenza A virus according to claim 1, comprising a PB2 protein that comprises at least one of the amino acid modifications selected from the group consisting of I504V, V560I, and A84S according to the numbering of SEQ ID NO:6.

3. A reassortant influenza A virus characterized in that it comprises:

at least two gene segments of seasonal or pandemic strain origin;

a PB1 gene segment of A/Texas/1/77 strain origin;

a PA gene segment of A/Puerto Rico/8/34 (PR8) origin coding for a PA protein amino acid modifications at positions 10, 275 and 682, according to the numbering of SEQ ID NO: 1; and a NP protein with at least one of the amino acid modifications selected from the group consisting of T130M, K236R, and R452K according to the numbering of SEQ ID NO: 10.

4. A reassortant influenza A virus according to claim 1, characterized in that the polynucleotide encoding the NS1 protein comprises a modification, substitution and/or deletion of at least one nucleotide.

5. A reassortant influenza A virus according to claim 1, characterized in that at least two gene segments are derived from an H5N1 strain.

6. A reassortant influenza A virus characterized in that it comprises:

at least two gene segments of seasonal or pandemic strain origin;

a PB1 gene segment of A/Texas/1/77 strain origin;

a PA gene segment of A/Puerto Rico/8/34 (PR8) origin coding for a PA protein comprising amino acid modifications N10S, P275L, and D682N according to the numbering of SEQ ID NO: 1;

a PB2 protein comprising amino acids modifications 1504V and/or V560I and/or A84S according to the numbering of SEQ ID NO: 6;

a NP protein with one or more amino acid modifications selected from the group consisting of T130M, K236R, and R452K according to the numbering of SEQ ID NO: 10; and an NS1 protein comprising a modification, substitution and/or deletion of at least one nucleotide.

7. A reassortant influenza A virus according to claim 5, wherein at least two gene segments are derived from an A/Vietnam/1203/04 strain.

8. A vaccine comprising the reassortant influenza virus of claim 6.

9. A vaccine according to claim 8 which is formulated for intranasal delivery.

10. A reassortant influenza A virus according to claim 3, comprising a PB2 protein that comprises at least one of the amino acid modifications selected from the group consisting of I504V, V560I, and A84S according to the numbering of SEQ ID NO:6.

11. A reassortant influenza A virus according to claim 3, characterized in that the polynucleotide encoding the NS1 protein comprises a modification, substitution and/or deletion of at least one nucleotide.

12. A reassortant influenza A virus according to claim 3, characterized in that at least two gene segments are derived from an H5N1 strain.

13. A reassortant influenza A virus according to claim 12, wherein the H5N1 strain is an A/Vietnam/1203/04 strain.

14. A vaccine comprising the reassortant influenza virus of claim 3.

15. A vaccine according to claim 14 which is formulated for intranasal delivery.

16. A vaccine comprising the reassortant influenza virus of claim 1.

17. A vaccine according to claim 16 which is formulated for intranasal delivery.

* * * * *